United States Patent [19]
Dew

[11] Patent Number: 4,672,969
[45] Date of Patent: Jun. 16, 1987

[54] LASER HEALING METHOD
[75] Inventor: Douglas Dew, Maitland, Fla.
[73] Assignee: Sonomo Corporation, Maitland, Fla.
[21] Appl. No.: 539,527
[22] Filed: Oct. 6, 1983
[51] Int. Cl.⁴ .............................................. A61N 5/06
[52] U.S. Cl. ................................. 128/397; 128/303.1
[58] Field of Search ............... 128/395, 396, 397, 398, 128/303.1, 6

[56] References Cited

U.S. PATENT DOCUMENTS 3,467,098  9/1969  Ayres ............................... 128/395 X
3,750,670  8/1973  Palanos et al. .................... 128/303.1
3,769,963  11/1973  Goldman et al. ................. 128/303.1
4,266,549  5/1981  Kimura ............................. 128/303.1

FOREIGN PATENT DOCUMENTS 2809007  9/1979  Fed. Rep. of Germany ...... 128/395
618116   6/1978  U.S.S.R. ............................... 128/395
886907  12/1981  U.S.S.R. ............................... 128/395

Primary Examiner—Anton O. Oechsle
Attorney, Agent, or Firm—Duckworth, Allen & Dyer

[57] ABSTRACT

The method and apparatus of the invention use laser emitted optical energy to effect wound closure and reconstruction of biological tissue. Optical energy is applied to produce thermal heating of biological tissue to a degree suitable for denaturing the tissue proteins such that the collagenous elements of the tissue form a "biological glue" to seal immediately and/or to reconstruct the tissue being heated. The collagenous glue is then reabsorbed by the body during the healing process. In a particularly advantageous method and apparatus, a Nd:YAG laser turned to 1.32 micrometers wavelength is used at low power levels to obtain deep tissue penetration with low thermal effect.

8 Claims, 4 Drawing Figures

THE ABSORPTION COEFFICIENT OF WATER BETWEEN
0.7 AND 10.0 μ. FROM BAVLY ET AL (1963)
COURTESY OF INFRARED SPECTRA. PERGAMON PRESS

THE ABSORPTION COEFFICIENT FOR HEMOGLOBIN
AS A FUNCTION OF WAVELENGTH

LASER HEALING METHOD

BACKGROUND OF THE INVENTION

This invention relates generally to methods and apparatus for closing wounds and more particularly, to a method and apparatus for applying optical energy to biological tissue whereby the tissue is converted to a collagenous, denatured protein substance which joins severed tissues and closes wounds.

Historically, suturing has been the accepted technique for rejoining severed tissues and closing wounds. Suturing has been achieved with a surgical needle and suturing thread, and more recently, with a variety of polymeric or metallic staples. The intended function of sutures is to hold the edges of the wounds against one another during healing so as to reduce discomfort, pain, scarring, and the time required for healing.

It is a problem with known suturing systems that since they are applied intermittently along a wound, they permit gaps in the wound between sutures to remain open thereby accepting dirt and bacteria. Moreover, in addition to producing a relatively high risk of infection and tissue rejection, such gaps between sutures are eventually filled in by keloid, which results in disfiguration and scarring. In addition, inflamation often results from the foreign body presence of the suture material.

It is an additional disadvantage of conventional sutures that they may slip in an axial direction thereby permitting relative motion between the tissues which are desired to be joined, and may loosen before the healing process has advanced sufficiently to maintain a tight closure of a wound. Thus, sutures must frequently be removed and replaced, thereby requiring multiple visits to a physician. There is a need, therefore, for a wound closure system which is uniform throughout the length of a wound.

A variety of cauterization and cryogenic techniques have been developed to reduce the flow of blood in an open wound, or a surgically-induced incision. Generally, cauterization is achieved by using intense heat to sear and seal the open ends of the tissues, such as vessels and capillaries. In known cauterization systems, heat is generated by resistance heating of a metallic probe which is subsequently applied to the tissue to be cauterized. Alternatively, undesired blood flow is discontinued by applying a cryogenic temperature which freezes the tissue. More recently, the medical field has utilized high intensity optical energy generated by one or more lasers to achieve cauterization which limits blood flow. In such known laser systems, the optical energy is applied in sufficient quantity to sear or burn the vessels. Laser cauterization is illustratively described in U.S. Pat. No. 4,122,853 to Michael R. Smith. These techniques, however, destroy the surrounding tissue leading to longer healing times, infection, and scarring.

Recent advances in the state of the art have produced cauterization with the use of ultrasonic energy which is converted to mechanical vibrations through a knife. Such a rapidly vibrating knife simultaneously cuts and closes off severed vessels. A system of the ultrasonic vibrational type is described in U.S. Pat. No. 3,794,040 which issued to Balamuth. known system, ultrasonic energy is applied to create heating of the vessels desired to be cauterized above room temperature, but below a temperature at which such vessel would sear. The heat thus produced causes hemeostasis, by denaturing of the proteins in the tissue to form a collagenous substances which performs as a glue to achieve the closure or bond. This technique, however, has not gained widespread use for delicate surgery because it requires bringing a vibrating probe into contact with the tissue to be affected. Moreover, ultrasonic energy is nonpreferentially absorbed and affects all of the surrounding tissue.

Optical energy generated by lasers has been applied in recent times to various medical and surgical purposes because the monochromatic and coherent nature of the light generated by lasers has been shown to have absorbency characteristics which vary with the nature of the illuminated tissue. Thus, for a given tissue type, the laser light may propagate through the tissue, substantially unattenuated, or may be almost entirely absorbed. Of course, the extent to which the tissue is heated, and ultimately destroyed, depends on the extent to which it absorbs the optical energy. It is generally preferred that the laser light be essentially transmissive in tissues which are desired not to be affected, and absorbed by the tissues which are to be affected. For example, when using lasers in fields which are wet with blood or water, it is desired that the optical energy not be absorbed by the water or blood, thereby permitting the laser energy to be directed specifically to the tissues desired to be affected. Such selective absorption also permits substantial time saving during an operation by obviating the need for cleaning and drying the operating field.

It is a further known advantage of a laser system that the optical energy can be delivered to the tissues desired to be operated upon in a precise location and at predeterminable energy levels. The precision with which the laser energy can be directed is enhanced by its ability to be guided by known thin optical fibers which permit the optical energy to be utilized within a body without requiring large incisions or to be inserted into the body through an endoscope. The optical fibers which conduct the laser-generated optical energy for performing the operation can be combined with other optical fibers which conduct light in the visible range, and further optical fibers which are of the image-transmissive type such that a surgeon may view and control an operation which is occurring within a body.

Ruby and argon lasers which are known to emit energy in the visible portion of the electromagnetic spectrum have been used successfully; particularly in the field of ophthalmology to reattach retinas to the underlying choroidea and to treat glaucoma by perforating anterior portions of the eye to relieve intraocular pressure. The ruby laser energy has a wavelength of 0.694 micrometers and, thus, appears red. The argon laser emits energy at 0.488 and 0.515 micrometers, thus, appearing blue-green. The ruby and argon laser beams are minimally absorbed by water, such as tissue water, but are intensely absorbed by the blood chromagen hemoglobin. Thus, the ruby and argon laser energy is poorly absorbed by nonpigmented tissue such as the cornea, lens, and vitreous humor of the eye, but is preferentially absorbed by the pigmented retina where it can then exert a thermal effect.

Another type of laser currently in surgical use is the carbon dioxide ($CO_2$) gas laser which emits a beam which is intensely absorbed by water. The wavelength of the $CO_2$ laser is 10.6 micrometers and therefore lies in the invisible, far infrared region of the electro-magnetic spectrum. Reference to FIG. IA shows that the absorption of energy by water in this part of the spectrum is so great that it is absorbed independently of tissue color by all soft tissues having a high water content. Thus, the $CO_2$ laser makes an excellent surgical scalpel and vaporizer. Since it is so completely absorbed, its depth of penetration is shallow and can be precisely controlled with respect to the surface of the tissue being operated upon. The $CO_2$ laser is frequently used for neuorological surgery where it is used to vaporize or coagulate neural tissue with minimal thermal damage to underlying tissues.

The fourth commonly used type of laser is the neodymium doped yttrium-aluminum-garnet (Nd:YAG) laser. The Nd:YAG laser has a predominant mode of operation at a wavelength of 1.06 micrometers in the near infrared region of the electromagnetic spectrum. Reference to FIG. IB shows that the Nd:YAG emission at 1 micrometers wavelength is absorbed to a greater extent by blood than by water making it useful for coagulating large bleeding vessels. The Nd:YAG at 1.06 $\mu$m laser energy has, for example, been transmitted through endoscopes to treat a variety of gastrointestinal bleeding lesions, such as esophogeal varices, peptic ulcers, and arteriovenous anomolies.

OBJECTS OF THE INVENTION

It is characteristic of all of these known uses of laser energy that the tissue thus exposed is destroyed by searing, charring, or vaporization. It is therefore an object of this invention to utilize laser energy either to heal or reconstruct tissue, rather than to destroy tissue.

It is also an object of this invention to replace surgical sutures or staples in wound closures by a technique which creates an immediate seal of the severed tissue, is faster, requires minimal surgical manipulation of tissue, reduces possibility of infection, and minimizes scarring.

It is another object of this invention to use the body's own tissue elements to form a seal or a bond between severed elements of tissue.

It is still another object to use electro-optical energy to form a collagenous bonding tissue which is similar in composition to the tissue from which it is produced.

It is yet a further object of the invention to provide wound closure and reconstruction, inter alia, of the following tissues: skin, nerve fiber, vascular tissues, reproductive tissue structures such as vas deferens or fallopian tubes, gastrointestinal tract, eye tissues, and tendons.

It is also a further object of the invention to provide the wound closure and reconstruction of the above-identified tissues quickly, with little or no scarring, and with minimal risk of infection.

It is a still further object of the invention to use laser energy having a low absorbance in a bloody or wet field to increase the utility of the laser within the normal operating fields.

It is still another object of the invention to utilize a laser energy which is not preferentially absorbed by either blood or water, thereby enabling a low temperature thermal effect to be produced upon a desired tissue with deeper penetration and with substantially reduced risk of damaging neighboring tissues.

It is also another object of the invention to provide a a method utilizing laser apparatus which is automated and portable for effecting closure of wounds and reconstruction of tissues.

SUMMARY OF THE INVENTION

The foregoing and other objects are achieved by this invention which provides a method for converting biological tissue into a collagenous substance for facilitating healing and wound closure. In accordance with a method aspect of the invention, a monochromatic beam of optical energy is generated at a wavelength in a range between 1.2 micrometers and 1.4 micrometers. Severed segments of a wound or tissue structure are brought into close proximity and a beam of optical energy is guided to the area of the juncture. Upon being illuminated by the beam of optical energy, the tissue in the vicinity of the wound is converted to a denatured proteinaceous collagenous substance which forms a biological glue which closes the wound.

The intensity of the optical energy is controlled such that the rate at which such optical energy is absorbed by the tissue in the vicinity of the wound and converts optical energy into thermal is within a range bounded by a minimum absorption rate at which the tissue is converted to a collagenous substance and a maximum absorption rate above which the water contained in the tissue boils. Generally, the intensity of the optical energy is controlled by attenuating the monochromatic beam in any of several known ways. The optical energy itself may be generated by a laser. Preferrably, the laser is of the Nd:YAG type which is operated at a secondary wavelength of approximately 1.32 micrometers. Ordinarily such Nd:YAG lasers operate at a fundamental wavelength of 1.06 micrometers.

It is intended that the invention not be limited to the particular wavelength of 1.32 micrometers or to a Nd:YAG lasing medium. It is a significant aspect of the invention that the particular wavelength of the optical energy be selected such that the optical energy is propagated without substantial attenuation through water and/or blood, but be absorbed in the biological tissue required to be repaired. Such substantially unattenuated transmission through water and blood simplifies surgical procedures by obviating the need for operating in a dry, clean field.

In accordance with the invention, the optical energy is produced by a source, illustratively a laser, having a wavelength between the above-noted 1.2 and 1.4 micrometers. The arrangement is further provided with a guide for directing the beam of optical energy to the wound in the tissue. Moreover, the arrangement is provided with a controller for controlling the intensity of the emitted optical energy. The energy is controlled to a level above which the tissue in the vicinity of the wound is converted to the collagenous substance, but not sufficient to boil water in the tissue being repaired.

In one embodiment of the invention, the arrangement is further provided with a lens which is adapted to produce a predeterminable divergence or convergence in the beam of optical energy as it is emitted from the optical arrangement. In this embodiment, the arrangement is provided with a distance measuring device whereby the size of the illuminated spot which is produced on the wound is predeterminable notwithstanding that the optical energy beam has a divergence characteristic upon being emitted.

In another embodiment of the invention, a marker beam of visible light is provided to illuminate and define the region in the wound where the beam of optical energy is to be applied. Such a marker beam is known for use in arrangements where, as here, the operating beam of optical energy is in the invisible region of the electromagnetic spectrum.

In a surgical system or apparatus for performing the method of the invention described above, a Nd:YAG laser which is tuned or is tunable to 1.32 microns is provided with a lens to focus the emitted beam into an optical fiber. The flexible optical fiber is then provided with a shutter and timer on a foot or hand operated switch, and is provided with a hand-piece for manual manipulation of the beam to the desired tissue. Various parameters such as power, beam spot size, time exposure, and laser mode are adjusted according to the desired usage. A microprocesser is further provided for sorting information relating to these parameters.

BRIEF DESCRIPTION OF THE DRAWINGS

These and other objects, features and advantages of the invention are more readily understood when read in conjunction with the following drawings wherein.

DETAILED DESCRIPTION OF THE INVENTION

Biological tissue comprises cell layers in a protein framework for tensile strength. All proteins are amino acids which have side chains which are disolvable either in water or fat. Naturation is a process wherein the amino acids fold over, always in the same configuration for each protein type, when the protein leaves the interior of a cell and is confronted with tissue water. In which case, the hydrophobic portion of a side chain folds to the interior of the molecule. The proteinaceous components of the tissue can be unfolded or denatured by the application of heat.

It has been discovered that application of optical energy to biological tissue, in an amount sufficient to generate enough heat to denature the proteinaceous, components, can be used to cause the body's own tissues to substantially reproduce the prior tissue structure at a lesion or severed tissue site. In a particularly advantageous embodiment of the invention, optical energy from a laser is applied to bring the temperature of biological tissue somewhere above room temperature, but below the boiling point of water; preferably above 45 degrees centigrade and particularly at about 60–70 degrees. Collagen, a major source of protein in the body, is denatured by application of energy so as to go into solution and form a "biological glue" to seal a lesion, anastomize a severed vessel, or reconstruct damaged tissue. When the source of heat is removed, the proteins begin to re-nature and form an approximate replication of the prior tissue structure. As the body heals, the so-called "biological glue" will be reabsorbed and replaced by natural tissue. It should be noted that the term lesion as used herein denotes a wound, whether formed accidently, intentionally, or by biological processes.

As can be appreciated, the application of heat, to form a collagenous seal to immediately close a lesion or anastomize a severed vessel has several other advantages. It accelerates healing time because blood supply to the effected tissue can be re-established immediately after operation. Moreover, little or no scarring is produced because no sutures are required. Sutures lead to destruction of tissue, allow the inclusion of foreign material in a wound thereby causing inflamation and/or infection, and permits gaps which are too wide for the body's natural rebuilding mechanism to bridge. Scar tissue is consequently generated as a result of a higher ratio of structural protein, i.e. collagen, to living cells in the vicinity of the lesion.

Figure 1A:
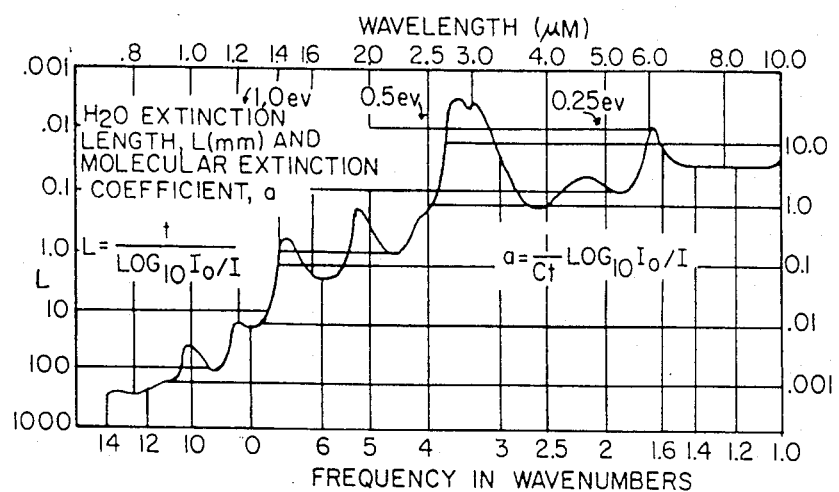
FIGS. 1A and 1B are graphs of the absorbance of optical energy by water and blood, respectively, plotted against the wavelength of applied energy.
Figure 1B:
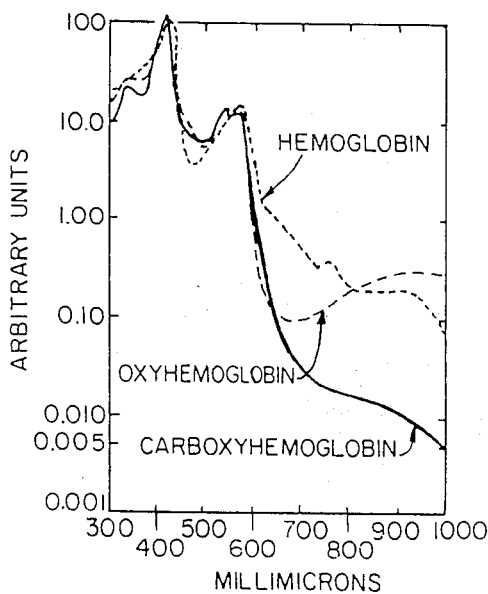

Optical energy is converted to heat in tissue which absorbs energy at that wavelength. Reference to FIG. 1B, shows that light in the visible range is readily absorbed by pigmented tissue, whereas light emitted in the far infrared, such as that emitted by a carbon dioxide laser, is highly absorbed in both water and blood. The Nd:YAG laser, in current use, emits energy primarily a wavelength at 1.06 micrometers and has more absorbance in blood than in water. This, therefore, requires that the operating field be cleared of blood which would absorb applied energy. Formation of a "biological glue" in order to effect repair of GI tract tissue, form skin wound closures, and repair and reconstruct tissue such as reproductive tissue, tendons, and vascular tissue requires optical energy having a wavelength which is relatively unattenuated in water and blood in order to penetrate through a thick layer of tissue at low power.

It was discovered that optical energy having a wavelength of 1.2 to 1.4 micrometers is relatively poorly absorbed by both water and blood. Moreover, the differential in absorptivity between water and blood is not so great as to cause one type to preferentially absorb optical energy in this range. In a particularly advantageous embodiment of the invention a commercially available Nd:YAG laser is used to generate optical energy having a wavelength of about 1.32 micrometers.

Figure 2:
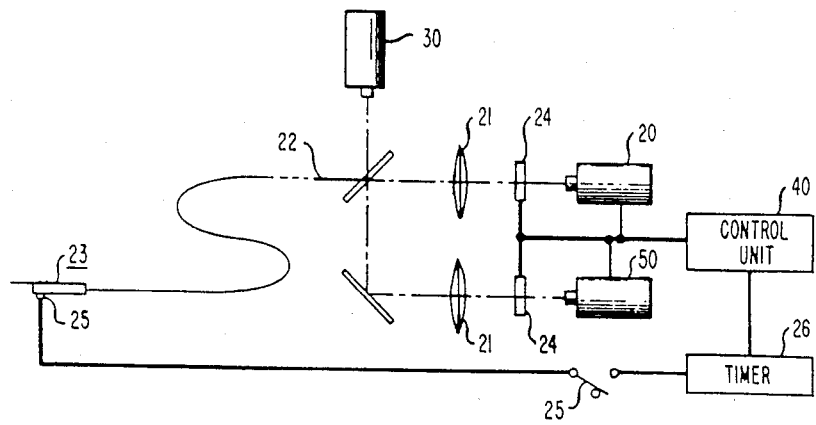
FIG. 2 is a block and schematic diagram of a laser surgical system for use in accordance with the invention.

FIG. 2. is a highly schematic representation of a laser surgical system for use in accordance with the invention. Laser 20 is preferably of the Nd:YAG crystalline variety wherein a yttrium-aluminum-garnet (YAG) rod is doped with Nd ions as the active light-producing element. As is known, laser 20 includes a resonant cavity for amplifying the emitted light and pumping means, such as a dc Krypton arc lamp, for supplying energy to create a population inversion of the normal energy state of Nd ions. Such a population inversion results in the stimulated emission of light in accordance with known laser principles.

Absent any tuning of the laser cavity, Nd:YAG lasers will always operate at a first and predominant mode of emission at a wavelength of approximately 1.06 micrometers. Nd:YAG lasers also emit light at a secondary wavelength of approximately 1.32 micrometers. Proper utilization of this secondary mode in laser operation requires the dominant emission, which has a greater amplitude than the secondary emission, to be suppressed. Typically, peak power output at this secondary emission level is 20–30% of the continuous wave peak power output at the dominant level. It is the secondary wavelength that is utilized in the method and apparatus of the invention.

As readily understood by persons skilled in the art, laser 20 includes a power station for activiating the pumping arc lamp and cooling means for the laser. A suitable Nd:YAG laser for use in this invention is produced by Control Laser Corporation, which is presently located at 11222 Astronaut Boulevard, Orlando, FL 32809.

A lens 21 is provided to focus the emerging coherent light beam from laser 20 into an optical fiber 22. Lens 21 may comprise a system of lenses. Optical fiber 22 can be of any known type, which efficiently transmits the desired wavelength. Optical fiber 22 provides a flexible conduit for guiding the optical energy from the laser into a hand-piece 23 which is manipulable by the physician. A shutter 24 is located, between laser 20 and lens 21. Hand-piece 23 contains a shutter switch 25 which controls release of the laser energy and which may be actuated by either the hand or the foot of the operator. A timer 26 is provided to control the shutter and, thereby, the duration of energy exposure. Hand-piece 23 may include a lens for focusing or defocusing the beam.

Figure 3:
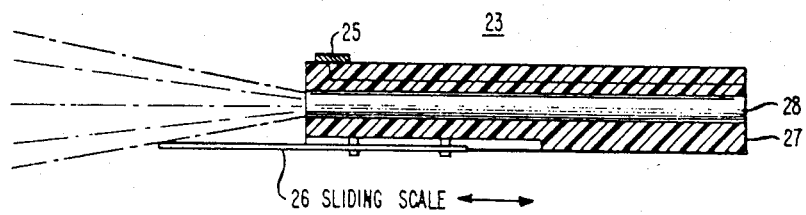
FIG. 3 is a schematic side view of a hand piece showing beam divergence to produce a beam spot size which varies with distance.

Advantageously, hand-piece 23 includes means to enable the physician to set the working distance between the tissue to be irradiated and the distal most end of the optical fiber of lens. In an illustrative embodiment, as shown in FIG. 3, a sliding scale 26 which cooperates with a protective case 27 on the end of optical fiber 28 controls the working distance, and hence, the diameter of the beam spot. As shown in FIG. 3, the divergence of the beam is used to control the diameter as the distance between the distal most end of the fiber and the tissue is increased or decreased.

The following electro-optical parameters require proper adjustment for each type of tissue: wavelength, spot or beam size, power, time exposure, and mode or beam geometry. In particular, the thermal effects on the tissue can be controlled by proper selection of the electro-optical parameters. Power density measures the energy concentration of the applied light beam and is typically expressed in watts per square centimeter area of the applied beam spot. Power density is directly related to the amount of heat that will be produced at a given absorptivity. If the wavelength of the applied beam is poorly absorbed, more heat can be generated by increasing the time of tissue exposure to the applied beam. Radiant exposure, expressed in joules per square centimeter, is a measure of the power density multiplied by the exposure time.

Means which are well known it the art are used to control the power output of laser 20. The power delivered to the tissue surface should be maintained under 10 watts for purposes of tissue reconstruction by laser 20 as described herein. The object is to deliver a specific amount of energy per volume of tissue. For a given spot size, which is related to the volume of tissue exposed, there are many combinations of power output and time exposure which will deliver equivalent amounts of energy. To wit, power delivered to the tissue typically ranges between 1 and 4 watts; although power delivered could go as high as 10 watts if the time exposure were reduced commensurately.

In the lowest order transmission mode, $TEM_{oo}$ specifically, a more concentrated beam results which can be used for cutting purposes at higher power output or for achieving very small beam spot size for tissue reconstruction. In the alternative, multimode transmission can be used for tissue reconstruction, but the beam spot size can not be as finely focussed as the $TEM_{oo}$ mode. However, if the beam is defocused, less power is delivered per unit area.

As will be understood, the selection of the various electro-optical parameters for each tissue type is made as a result of skill and experience; but is determinable without undue experimentation by one of ordinary skill in the art.

In a particularly advantageous embodiment, data relating to appropriate settings of electro-optical parameters for various tissue types can be coded on a computer memory device, such as floppy disc or programmable read-only memory computer chip. Thus, control unit 40 can be provided to adjust automatically the time exposure, power level, and display the proper spot size upon input of tissue type and the operating conditions by the physician or surgeon.

A marker laser 30, illustratively a low-power helium-neon laser, is coaligned with the infrared beam of laser 20. Laser 30, however, can be of any type which emits radiation in the visible range of the electromagnetic spectrum. The power rating of the helium-neon marker laser 30 is between 1–5 mWatts. Marker laser 30 can be arranged so that its focal point coincides with that of the main operating laser 20 by any known technique.

As an optional feature, in order to permit the use of the laser apparatus of FIG. 2 on very thin tissue or tissue upon which only surface heating is desired, such as epineurium of nerve tissue, an auxiliary source of optical energy 50 can be incorporated into the apparatus to emit radiation having a wavelength which is intensely absorbed by biological tissue. A carbon dioxide laser, of any known type, would be a suitable auxiliary source, Source 50 is also preferrably arranged so as to have its output beam coincide with the beam from marker laser 30.

It should be further pointed out that the 1.06 micrometer wavelength of the Nd:YAG laser 20 can be selected by means which are well known in the art for the purposes of tissue coagulation and wound hemostasis, as desired.

In an illustrative embodiment, the apparatus of FIG. 2 is used for skin closure at a lesion site. The tissue edges of the lesion are brought into close approximation by manual manipulation, for example. Hand-piece 23 is positioned above the lesion at such a distance as to produce the desired beam spot size. The power, spot size, and time exposure are adjusted so as to heat the tissue above 45 degrees centigrade, but below the boiling point of water (100 degrees centigrade). Typical spot sizes range from 0.1 mm to 1.0 mm for levels of power delivered to the tissue ranging from 1 to 5 watts, and time durations ranging from 0.05 to 5.0 seconds. When the optical energy of laser 20 at 1.32 micrometers is released on the lesion site, with the electrooptical parameters adjusted as hereinabove suggested, the tissue at the lesion site is heated to a temperature sufficient to cause denaturization of the tissue proteins to the depth necessary to reconstruct the tissue in the lesion irrespective of whether the operating field is bloody or wet. These same electro-optical parameters may be applied to the reconstruction of many soft tissues such as vascular structures, tendon, vas deferens, fallopian tubes, gastro-intestinal tract, dura, and sclera. With a modification of the level of power delivered to the tissue under repair, cartilage and tympanic membranes can be repaired in accordance with the invention described hereinabove.

The above-described embodiments are provided for the purpose of illustration and are not to be construed as limiting. Other modifications and adaptations can be made by those of skill in the art without departing from the spirit and scope of the invention. In particular, the laser energy can be transmitted to the patient treatment site by an articulated arm with mirrors or it can be transmitted to the interior of a patient by endoscope. Moreover, materials other than neodymium-doped crystalline yttrium-aluminum-garnet can be used as a lasing medium to generate optical energy at the desired wavelengths.

What is claimed is:

1. A method of reconstructing biological tissue wherein a proteinaceous framework is formed from denatured protein in the vicinity of the tissue being reconstructed, which framework approximates the biological tissue being reconstructed, the method comprising the step of non-destructively applying optical energy to the biological tissue at such a wave-length and at such power dissipation in the tissue as to cause the amount of optical energy absorbed and converted to heat to be within a range bounded by a minimum absorption rate at which tissue is converted to a collagenous substance and a maximum absorption rate at which the water in the tissue would boil, so as to cause proteinaceous elements of the biological tissue to denature.

2. The method of claim 1 wherein said wavelength is in the range of 1.2 to 1.4 micrometers.

3. The method of claim 1 wherein said power is greater than 0 but no greater than 10 watts per square centimeter.

4. The method of claim 2 wherein said wavelength is about 1.32 micrometers and said step of applying comprises applying optical energy generated at a secondary wavelength of a Nd:YAG laser, whereby the optical energy is propagated into tissue without substantial attenuation through blood and water.

5. A method of healing a lesion in biological tissue of the type having proteinaceous elements, the method comprising the step of forming a seal at said lesion by applying optical energy having a wavelength from about 1.2 to 1.4 micrometers to said lesion, and at a level of power such that the optical energy absorbed and converted to heat in the tissue is no greater than 10 watts per square centimeter, so as to cause the proteinaceous elements of the biological tissue in the vicinity of said lesion to denature, thereby forming a collagenous seal at said lesion.

6. The method of claim 5 wherein the lesion comprises at least two segments of biological tissue and said method further comprises bringing said at lest two segments of tissue into close proximity and guiding said optical energy into the area of their junction.

7. The method of claim 5 wherein said optical energy is in the form of a monochromatic laser beam.

8. The method of claim 7 wherein said laser beam is generated by a Nd:YAG laser which is tuned to emit optical energy at its secondary wavelength of about 1.32 micrometers.

* * * * *